US00PP21016P2

(12) United States Plant Patent
Saul

(10) Patent No.: US PP21,016 P2
(45) Date of Patent: May 25, 2010

(54) *ALTERNANTHERA* PLANT NAMED 'RASPBERRY RUM'

(50) Latin Name: *Alternanthera ficoidea*
Varietal Denomination: Raspberry Rum

(75) Inventor: Robert Saul, Atlanta, GA (US)

(73) Assignee: Itsaul Plants LLC, Alpharetta, GA (US)

( * ) Notice: Subject to any disclaimer, the term of this patent is extended or adjusted under 35 U.S.C. 154(b) by 0 days.

(21) Appl. No.: 12/321,739

(22) Filed: Jan. 23, 2009

(51) Int. Cl.
*A01H 5/00* (2006.01)

(52) U.S. Cl. ..... Plt./373

(58) Field of Classification Search ..... Plt./373, Plt./263
See application file for complete search history.

*Primary Examiner*—Susan B McCormick Ewoldt
(74) *Attorney, Agent, or Firm*—C. A. Whealy

(57) ABSTRACT

A new and distinct cultivar of *Alternanthera* plant named 'Raspberry Rum', characterized by its upright to outwardly spreading and mounding plant habit; freely branching habit; dense and bushy growth habit; strong and healthy leaves; leaves that are hot pink and brown in color; good garden performance; and resistance to leaf spot pathogens.

1 Drawing Sheet

Botanical designation: *Alternanthera ficoidea.*
Cultivar denomination: 'Raspberry Rum'.

BACKGROUND OF THE INVENTION

The present invention relates to a new and distinct cultivar of *Alternanthera* plant, botanically known as *Alternanthera ficoidea* and hereinafter referred to by the name 'Raspberry Rum'.

The new *Alternanthera* plant is a naturally-occurring branch mutation of *Alternanthera ficoidea* 'Cognac', disclosed in U.S. Plant Pat. No. 16,411. The new *Alternanthera* plant was discovered and selected by the Inventor from within a population of plants of 'Cognac' in a controlled greenhouse environment in Alpharetta, Ga. during the summer of 2005.

Asexual reproduction of the new *Alternanthera* plant by vegetative cuttings in a controlled greenhouse environment in Alpharetta, Ga. since July, 2005, has shown that the unique features of this new *Alternanthera* plant are stable and reproduced true to type in successive generations.

SUMMARY OF THE INVENTION

Plants of the new *Alternanthera* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Raspberry Rum'. These characteristics in combination distinguish 'Raspberry Rum' as a new and distinct cultivar of *Alternanthera:*

1. Upright to outwardly spreading and mounding plant habit.
2. Freely branching habit; dense and bushy growth habit.
3. Strong and healthy leaves.
4. Leaves that are hot pink and brown in color.
5. Good garden performance.
6. Resistant to leaf spot pathogens.

Plants of the new *Alternanthera* differ primarily from plants of the parent, 'Cognac', in leaf color as plants of 'Cognac' have brown-colored leaves.

Plants of the new *Alternanthera* can be compared to plants of *Alternanthera ficoidea* 'Grenadine', disclosed in U.S. Plant Pat. No. 16,442. In side-by-side comparisons conducted in Alpharetta, Ga., plants of the new *Alternanthera* differed from plants of 'Grenadine' in the following characteristics:

1. Plants of the new *Alternanthera* were more upright than and not as mounding as plants of 'Grenadine'.
2. Plants of the new *Alternanthera* had larger leaves than plants of 'Grenadine'.
3. Plants of the new *Alternanthera* and 'Grenadine' differed in leaf color as plants of 'Grenadine' had brown and red purple-colored leaves.

Plants of the new *Alternanthera* can be compared to plants of *Alternanthera ficoidea*'Partytime', disclosed in U.S. Plant Pat. No. 14,789. In side-by-side comparisons conducted in Alpharetta, Ga., plants of the new *Alternanthera* differed from plants of 'Partytime' in the following characteristics:

1. Plants of the new *Alternanthera* were more upright than and not as trailing as plants of 'Partytime'.
2. Plants of the new *Alternanthera* and 'Partytime' differed in leaf color as plants of 'Partytime' had green, creamy white and red purple-colored leaves.

BRIEF DESCRIPTION OF THE PHOTOGRAPH

The accompanying colored photograph illustrates the overall appearance of the new *Alternanthera,* showing the colors as true as it is reasonably possible to obtain in colored reproductions of this type. Colors in the photograph may differ slightly from the color values cited in the detailed botanical description which accurately describe the colors of the new *Alternanthera.* The photograph comprises a top perspective view of a typical plant of 'Raspberry Rum' grown in a ground bed in an outdoor nursery.

DETAILED BOTANICAL DESCRIPTION

The aforementioned photograph and following observations, measurements and values describe plants grown during the summer in an outdoor nursery in north central Texas. Plants had been growing for six months in the outdoor nursery when the photograph and description were taken. In the following description, color references are made to The Royal Horticultural Society Colour Chart, 2001 Edition, except where general terms of ordinary dictionary significance are used.

Botanical classification: *Alternanthera ficoidea* 'Raspberry Rum'.

Parentage: Naturally-occurring branch mutation of *Alternanthera ficoidea* 'Cognac', disclosed in U.S. Plant Pat. No. 16,411.

Propagation:

*Type.*—By vegetative cuttings.

*Time to initiate roots, summer.*—About twelve days at 24° C.

*Time to initiate roots, winter.*—About two weeks at 18° C.

*Time to produce a rooted young plant, summer.*—About four weeks at 24° C. to 29° C.

*Time to produce a rooted young plant, winter.*—About five weeks at 18° C.

*Root description.*—Thin, fibrous; white in color.

*Rooting habit.*—Freely branching; dense.

Plant description:

*Plant form and growth habit.*—Upright to outwardly spreading plant and mounding habit; herbaceous subshrub; short internodes; densely foliated; moderately vigorous growth rate.

*Branching habit.*—Freely basal branching habit with lateral branches potentially forming at every internode.

*Plant height.*—About 33 cm.

*Plant diameter.*—About 52 cm.

*Lateral branch description.*—Length: About 38 cm. Diameter: About 4 mm. Internode length: About 3.1 cm. Strength: Strong; flexible. Texture: Smooth, glabrous. Color: Close to 152C flushed with close to 59A.

*Leaf description.*—Arrangement: Opposite; simple; strong and healthy leaves. Length: About 6 cm. Width: About 4 cm. Shape: Ovate. Apex: Acuminate. Base: Cordate with truncate tendencies. Margin: Entire.

*Texture, upper and lower surfaces.*—Smooth, glabrous; rugose.

*Venation.*—Pinnate.

*Color.*—Developing leaves, upper surface: Close to 200A with random sectors of between 58A and 61A. Developing leaves, lower surface: Close to 200B with random sectors of between dulled 58A and dulled 61A. Fully expanded leaves, upper surface: Close to 200A with random sectors of between 58A and 61A. Midvein, close to 59A; lateral veins, similar to leaf surface color. Developing leaves, lower surface: Between 200B and 183B flushed with close to 59A. Midvein, close to 58A; lateral veins, similar to leaf surface color.

*Petiole.*—Length: About 2.2 cm. Diameter: About 1.5 mm. Texture, upper and lower surface: Smooth, glabrous. Color, upper surface: Close to 59A. Color, lower surface: Close to 58A.

Flower description: Flower development as not been observed on plants of the new *Alternanthera*.

Disease/pest resistance: Plants of the new *Alternanthera* have been observed to be resistant to bacterial and fungal leaf spot pathogens. Plants of the new *Alternanthera* have not been observed to be resistant to pests and other pathogens common to *Alternanthera*.

Garden performance: Plants of the new *Alternanthera* have been observed to have good garden performance and tolerate rain, wind and temperatures ranging from about 4° C. to about 43° C.

It is claimed:

1. A new and distinct *Alternanthera* plant named 'Raspberry Rum' as illustrated and described.

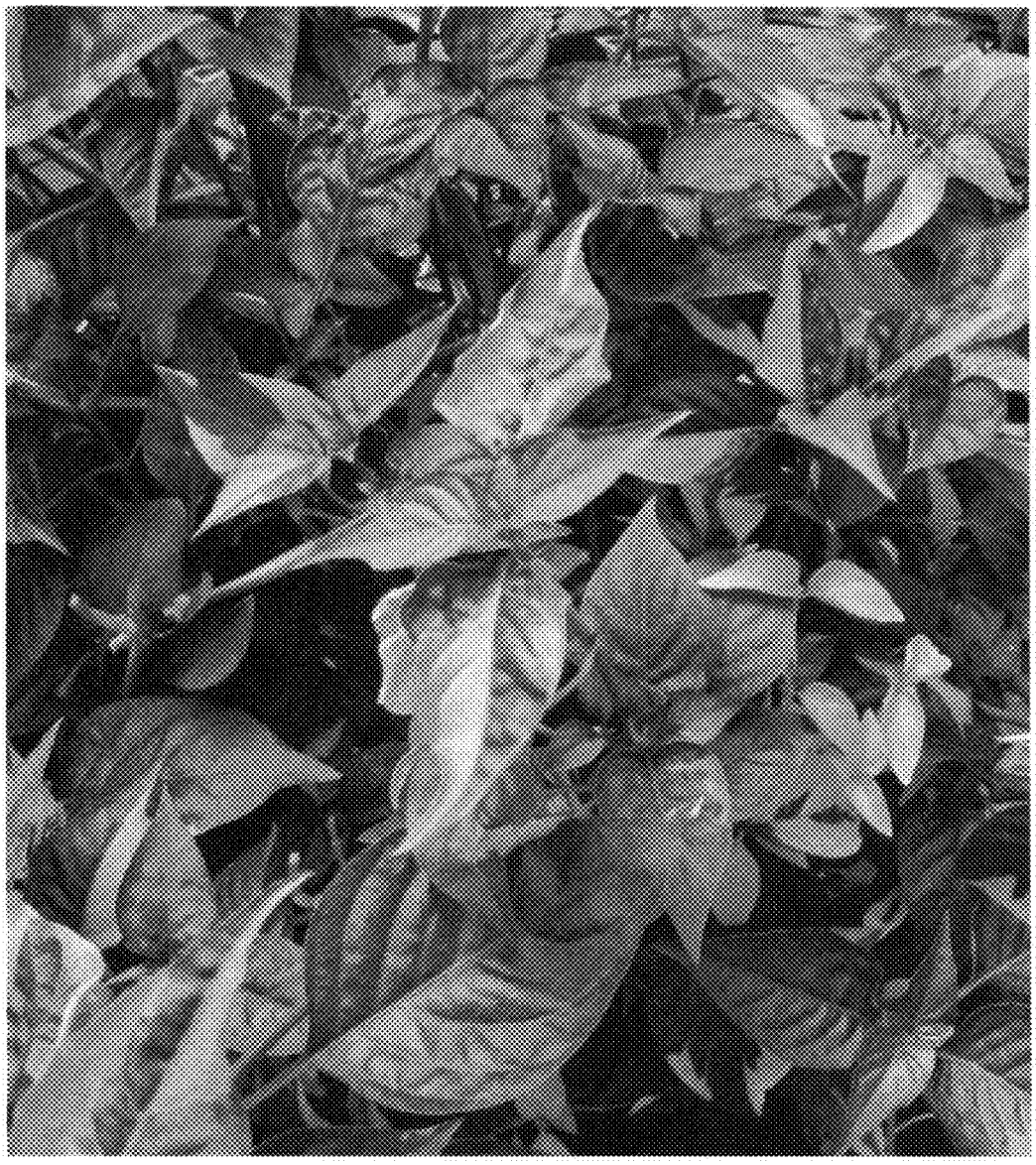

* * * * *